US009486631B2

(12) United States Patent
Libbus et al.

(10) Patent No.: US 9,486,631 B2
(45) Date of Patent: Nov. 8, 2016

(54) VAGAL NERVE STIMULATOR WITH MODE SWITCHING

(71) Applicant: Cardiac Pacemakers, Inc., St. Paul, MN (US)

(72) Inventors: Imad Libbus, St. Paul, MN (US); Andrew P. Kramer, Marine on St. Croix, MN (US); William J. Linder, Golden Valley, MN (US); Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/318,785

(22) Filed: Jun. 30, 2014

(65) Prior Publication Data

US 2014/0316487 A1 Oct. 23, 2014

Related U.S. Application Data

(60) Continuation of application No. 13/909,777, filed on Jun. 4, 2013, now Pat. No. 8,768,456, which is a division of application No. 11/137,038, filed on May 25, 2005, now Pat. No. 8,473,049.

(51) Int. Cl.
*A61N 1/36* (2006.01)
*A61N 1/368* (2006.01)

(52) U.S. Cl.
CPC ........ *A61N 1/36053* (2013.01); *A61N 1/36114* (2013.01); *A61N 1/36128* (2013.01); *A61N 1/36135* (2013.01); *A61N 1/3605* (2013.01); *A61N 1/3688* (2013.01)

(58) Field of Classification Search
CPC ................... A61N 1/36053; A61N 1/36114
USPC ............................................................ 607/3
See application file for complete search history.

(56) References Cited

U.S. PATENT DOCUMENTS 4,592,359 A 6/1986 Galbraith
4,699,143 A * 10/1987 Dufresne ........... A61N 1/36014
607/46

(Continued)

FOREIGN PATENT DOCUMENTS

NO WO-03099377 A1 12/2003
WO WO-2006127248 A1 11/2006

OTHER PUBLICATIONS

U.S. Appl. No. 11/137,038, Appeal Brief filed May 4, 2009, 34 pgs.

(Continued)

*Primary Examiner* — Eric D. Bertram
(74) *Attorney, Agent, or Firm* — Schwegman Lundberg & Woessner, P. A.

(57) ABSTRACT

Various aspects of the present subject matter relate to an implantable device. Various device embodiments comprise at least one port to connect to at least one lead with at least electrode, stimulation circuitry connected to the at least one port and adapted to provide at least one neural stimulation therapy to at least one neural stimulation target using the at least one electrode, sensing circuitry connected to the at least one port and adapted to provide a sensed signal, and a controller connected to the stimulation circuitry to provide the at least one neural stimulation therapy and to the sensing circuitry to receive the sensed signal. In response to a triggering event, the controller is adapted to switch between at least two modes. Other aspects and embodiments are provided herein.

20 Claims, 10 Drawing Sheets

(56) References Cited

U.S. PATENT DOCUMENTS

| | | |
|---|---|---|
| 5,330,507 A | 7/1994 | Schwartz |
| 6,272,377 B1 | 8/2001 | Sweeney et al. |
| 6,400,982 B2 | 6/2002 | Sweeney et al. |
| 6,463,328 B1 | 10/2002 | John |
| 6,466,822 B1 | 10/2002 | Pless |
| 6,493,586 B1 | 12/2002 | Stahmann et al. |
| 6,690,974 B2 | 2/2004 | Archer et al. |
| 6,751,505 B1 | 6/2004 | Van Den Honert et al. |
| 6,889,079 B2 | 5/2005 | Bocek et al. |
| 6,928,324 B2 | 8/2005 | Park et al. |
| 7,039,466 B1 | 5/2006 | Harrison et al. |
| 7,260,431 B2 | 8/2007 | Libbus et al. |
| 8,406,876 B2 | 3/2013 | McCabe |
| 8,473,049 B2* | 6/2013 | Libbus et al. ............ 607/3 |
| 8,768,456 B2* | 7/2014 | Libbus et al. ............ 607/3 |
| 2001/0020136 A1 | 9/2001 | Sweeney et al. |
| 2002/0016550 A1 | 2/2002 | Sweeney et al. |
| 2002/0072770 A1 | 6/2002 | Pless |
| 2002/0077670 A1 | 6/2002 | Archer et al. |
| 2002/0169485 A1 | 11/2002 | Pless et al. |
| 2003/0074039 A1 | 4/2003 | Puskas |
| 2003/0144711 A1 | 7/2003 | Pless et al. |
| 2003/0153953 A1 | 8/2003 | Park et al. |
| 2003/0212445 A1 | 11/2003 | Weinberg |
| 2004/0002635 A1 | 1/2004 | Hargrove et al. |
| 2004/0024429 A1 | 2/2004 | Daly |
| 2004/0082980 A1 | 4/2004 | Mouine et al. |
| 2004/0102820 A1 | 5/2004 | Mouine et al. |
| 2004/0138724 A1 | 7/2004 | Sieracki et al. |
| 2005/0010263 A1 | 1/2005 | Schauerte |
| 2005/0027321 A1 | 2/2005 | Ferek-Petric |
| 2005/0060001 A1 | 3/2005 | Singhal et al. |
| 2005/0075690 A1 | 4/2005 | Toy et al. |
| 2005/0096705 A1 | 5/2005 | Pastore et al. |
| 2005/0107844 A1 | 5/2005 | Van Den Honert et al. |
| 2005/0149128 A1 | 7/2005 | Heil et al. |
| 2005/0149130 A1 | 7/2005 | Libbus |
| 2005/0182389 A1 | 8/2005 | LaPorte et al. |
| 2005/0261741 A1 | 11/2005 | Libbus et al. |
| 2005/0267542 A1* | 12/2005 | David ............ A61B 5/412 607/17 |
| 2006/0020297 A1 | 1/2006 | Gerber et al. |
| 2006/0079945 A1 | 4/2006 | Libbus |
| 2006/0095080 A1 | 5/2006 | Libbus et al. |
| 2006/0106429 A1 | 5/2006 | Libbus et al. |
| 2006/0111632 A1 | 5/2006 | Chen |
| 2006/0116737 A1 | 6/2006 | Libbus |
| 2006/0122675 A1 | 6/2006 | Libbus et al. |
| 2006/0206153 A1 | 9/2006 | Libbus et al. |
| 2006/0206154 A1 | 9/2006 | Moffitt et al. |
| 2006/0206158 A1 | 9/2006 | Wu et al. |
| 2006/0206159 A1 | 9/2006 | Moffitt et al. |
| 2006/0217772 A1 | 9/2006 | Libbus et al. |
| 2006/0224202 A1 | 10/2006 | Moffitt et al. |
| 2006/0229677 A1 | 10/2006 | Moffitt et al. |
| 2006/0241699 A1 | 10/2006 | Libbus et al. |
| 2006/0259083 A1 | 11/2006 | Libbus et al. |
| 2008/0015648 A1 | 1/2008 | Libbus et al. |
| 2013/0267893 A1 | 10/2013 | Libbus et al. |

OTHER PUBLICATIONS

U.S. Appl. No. 11/137,038, Appeal Brief filed Jan. 13, 2010, 35 pgs.

U.S. Appl. No. 11/137,038, Preliminary Amendment filed Jun. 20, 2006, 11 pgs.

U.S. Appl. No. 11/137,038, Response filed May 15, 2008 to Non Final Office Action mailed Feb. 5, 2008, 13 pgs.

U.S. Appl. No. 11/137,038, Appeal Decision mailed Dec. 11, 2012, 23 pgs.

U.S. Appl. No. 11/137,038, Examiner's Answer mailed Mar. 31, 2010, 10 pgs.

U.S. Appl. No. 11/137,038, Final Office Action mailed Aug. 14, 2009, 10 pgs.

U.S. Appl. No. 11/137,038, Final Office Action mailed Aug. 29, 2008, FOAR, 10 pgs.

U.S. Appl. No. 11/137,038, Non-Final Office Action mailed Feb. 5, 2008, OARN, 8 pgs.

U.S. Appl. No. 11/137,038, Notice of Allowance mailed Feb. 25, 2013, 9 pgs.

U.S. Appl. No. 11/137,038, Pre-Appeal Brief request for Review filed Jan. 29, 2009, 5 pgs.

U.S. Appl. No. 11/137,038, Response filed Dec. 13, 2007 to Restriction Requirement Nov. 15, 2007, 12 pgs.

U.S. Appl. No. 11/137,038, Restriction Requirement mailed Nov. 15, 2007, 8 pgs.

U.S. Appl. No. 13/909,777, Non Final Office Action mailed Oct. 28, 2013, 8 pgs.

U.S. Appl. No. 13/909,777, Notice of Allowance mailed Feb. 20, 2014, 8 pgs.

U.S. Appl. No. 13/909,777, Response filed Jan. 28, 2014 to Non Final Office Action mailed Oct. 28, 2014, 8 pgs.

U.S. Appl. No. 13/909,777, Response filed Oct. 10, 2013 to Restriction Requirement mailed Sep. 11, 2013, 8 pgs.

U.S. Appl. No. 13/909,777, Restriction Requirement mailed Sep. 11, 2013, 6 pgs.

Bilgutay A M, et al., "A new concept in the treatment of hypertension utilizing an implantable electronic device: "Baropacer"", Trans Am Soc Artif Intern Organs., 10, (1964), 387-395.

Li, M., et al., "Vagal nerve stimulation markedly improves long-term survival after chronic heart failure in rats", Circulation, 109(1), (2004), 120-124.

Sigurdsson, A., et al., "The Role of Neurohormonal Activation in Chronic Heart Failure and Postrnyocardial Infarction", American Heart Journal, 132(1, Part 2), (Jul. 1996), 229-234.

Vanoli, E., et al, "Vagal Stimulation and Prevention of Sudden Death in Conscious Dogs With a Healed Myocardial Infarction", Circulation Research, 68(5), (May 1991), 1471-1481.

U.S. Appl. No. 13/798,684, filed Mar. 13, 2013, Closed Loop Neural Stimulation Synchronized to Cardiac Cycles.

* cited by examiner

VAGAL NERVE STIMULATOR WITH MODE SWITCHING

CLAIM OF PRIORITY

This application is a continuation of U.S. application Ser. No. 13/909,777, filed Jun. 4, 2013, now issued as U.S. Pat. No. 8,768,456, which is a division of U.S. application Ser. No. 11/137,038, filed May 25, 2005, now issued as U.S. Pat. No. 8,473,049, which is hereby incorporated by reference in its entirety.

TECHNICAL FIELD

This application relates generally to medical devices and, more particularly, to implantable devices capable of providing neural stimulation.

BACKGROUND

Neural stimulation has been the subject of a number of studies and has been proposed for several therapies. Direct electrical stimulation of parasympathetic nerves can activate the baroreflex, inducing a reduction of sympathetic nerve activity and reducing blood pressure by decreasing vascular resistance. Sympathetic inhibition, as well as parasympathetic activation, have been associated with reduced arrhythmia vulnerability following a myocardial infarction, presumably by increasing collateral perfusion of the acutely ischemic myocardium and decreasing myocardial damage. Modulation of the sympathetic and parasympathetic nervous system with neural stimulation has been shown to have positive clinical benefits, such as protecting the myocardium from further remodeling and predisposition to fatal arrhythmias following a myocardial infarction.

SUMMARY

Various aspects of the present subject matter relate to an implantable device. Various device embodiments comprise at least one port to connect to at least one lead with at least electrode, stimulation circuitry, sensing circuitry and a controller. The stimulation circuitry is connected to the at least one port and adapted to provide at least one neural stimulation therapy to at least one neural stimulation target using the at least one electrode. The sensing circuitry is connected to the at least one port and adapted to provide a sensed signal. The controller is connected to the stimulation circuitry to provide the at least one neural stimulation therapy and to the sensing circuitry. In response to a triggering event, the controller is adapted to switch between at least two modes.

In response to a triggering event, the controller of various device embodiments is adapted to switch between at least two modes selected from the group consisting of a stimulation and sensing mode, a stimulation mode, and a sensing mode. In the stimulation and sensing mode, the neural stimulation therapy is provided using a sensed signal. In the stimulation mode, the neural stimulation therapy is provided without using the sensed signal. In the sensing mode, the neural stimulation therapy is not provided to the neural stimulation target.

In response to a triggering event, the controller of various device embodiments is adapted to switch between at least two modes to switch neural stimulation targets. In response to a triggering event, the controller of various device embodiments is adapted to switch between at least two modes to switch sensing sites from which to provide the sensed signal, to switch sensed parameters used to provide the sensed signal, or to switch both sensing sites and sensed parameters.

Various system embodiments comprise at least one port to connect to at least one lead with at least electrode, at least one stimulation circuit connected to the at least one port and adapted to provide at least one neural stimulation therapy to at least one neural stimulation target and to provide a cardiac rhythm management (CRM) therapy using the at least one electrode, at least one sensing circuit connected to the at least one port and adapted to provide a sensed signal, and a controller connected to the at least one stimulation circuit to provide the at least one neural stimulation therapy and the CRM therapy and to the sensing circuitry. In response to a triggering event the controller is adapted to switch between at least two modes selected from the group consisting of a neural stimulation therapy mode, a CRM therapy mode, and a neural stimulation and CRM therapy mode. In the neural stimulation therapy mode, the neural stimulation therapy is provided to the neural target. In the CRM therapy mode, the CRM therapy is provided. In the neural stimulation and CRM therapy mode, the neural stimulation therapy is provided to the neural stimulation target and the CRM therapy is provided.

In various device embodiments, the controller is adapted to operate the device in at least two modes and to switch modes in response to a triggering event. The at least two modes are provided in at least one set of modes selected from the group consisting of a set of operation modes, a set of stimulation site modes and a set of feedback modes. In some embodiments, the group further consists of a set of therapy modes such that the device is able to switch between or among two or more therapy modes. Examples of operation modes includes a mode to provide neural stimulation and sensing, a mode to provide neural stimulation without sensing, and a mode to provide sensing without neural stimulation. Examples of stimulation site modes includes a mode to provide neural stimulation to a first neural stimulation site(s) or target(s) and a mode to provide neural stimulation to a second neural stimulation site(s) or target(s). Examples of feedback modes includes a mode to sense from a first site and a mode to sense from a second site, and also includes a mode to sense a first parameter and a mode to sense a second parameter. Examples of therapy modes include neural stimulation therapy, CRM therapy, drug therapy, and combinations thereof.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

Figure 1:
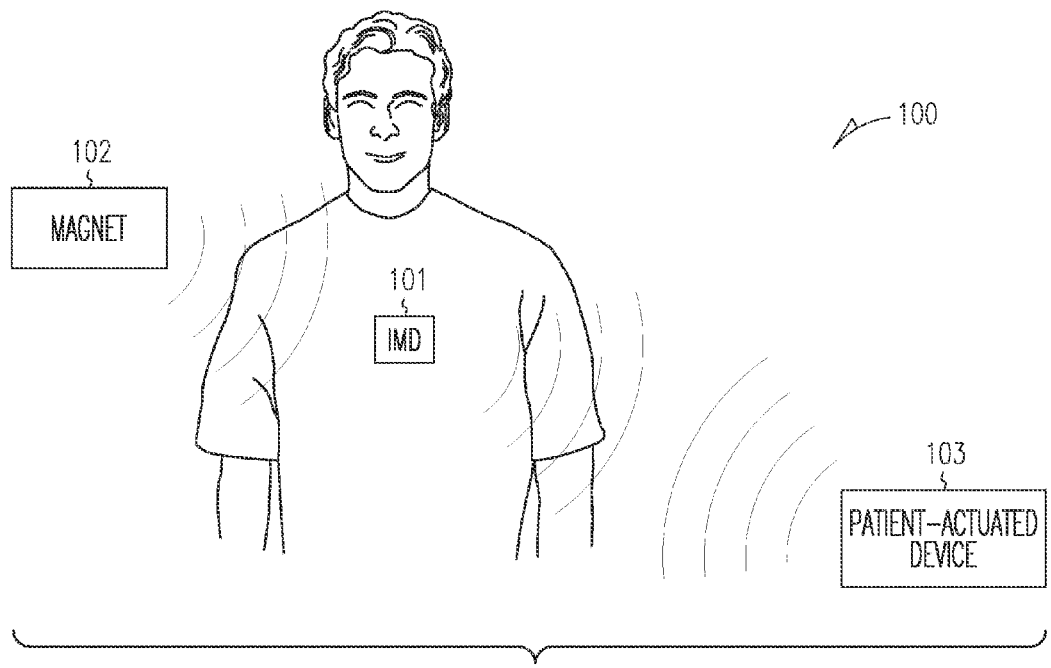
FIG. 1 illustrates an embodiment of a system with an implantable medical device (IMD).

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The present subject matter relates to an implantable device that provides neural stimulation. In various embodiments, the device also provides neural sensing. In addition to neural stimulation therapy, various device embodiments are adapted to provide cardiac rhythm management (CRM) therapy such as pacing, defibrillation, cardiac resynchronization therapy (CRT) or a combination of pacing, defibrillation and CRT. In addition to neural stimulation therapy, various device embodiments are adapted to provide drug therapy. Some embodiments are adapted to provide various combinations of neural stimulation therapy, CRM therapy and drug therapy. Some therapeutic mode switches include switching among CRM therapies to treat various conditions such as atrial fibrillation, bradycardia and ventricular tachycardia.

The device operates using at least two modes, and has the capability to switch between different modes in response to a triggering event. A variety of mode types are capable of being switched. Some embodiments change modes within a set of operation modes. For example, the device detects the presence of an unacceptably high level of electrical interference, and switches to a "stimulate only" mode in which neural sensing is disabled, or to a "sense only" mode in which neural stimulation is disabled. Some embodiments change modes to change the site or sites of neural stimulation. For example, the device reverts to an alternate lead or electrode in response to a detected electrode failure. Some embodiments change modes within a set of feedback modes to change sensing sites and/or sensed parameters. Some embodiments are adapted to switch between or among various combinations of neural stimulation therapy, CRM therapy, and drug therapy.

The triggering event to switch modes can be automatic or patient-actuated. Examples of patient-actuated triggers include a magnet placed proximate to the implantable device and an external controller unit. For example, some device embodiments switch to a "sense only" mode in response to an external magnet, providing an emergency shut-off mechanism. Some device embodiments toggle between two or among three or more different modes of operation in response to an external magnet. Some device embodiments allow the user (e.g. patient) to select the mode of operation with an external controller unit. An example of an automatic triggering event includes detected noise, where the device detects the presence of an unacceptably high level of electrical interference, and switches to a "stimulate only" mode in which neural sensing is disabled, or to a "sense only" mode in which neural stimulation is disabled.

FIG. 1 illustrates an embodiment of a system 100 with an implantable medical device (IMD) 101. The MID is adapted to switch modes in response to a triggering event. According to various embodiments, the triggering event is an automatic event, a patient-actuated event, or a combination of an automatic and patient-actuated events. Examples of automatic triggering events include a detected device change such as a detected electrode failure, an End Of Life (EOL) determination for a battery to power the device, a detected lead failure, an environmental change like a detected electrical interference that is capable of interfering with the sensed signal or the application of another therapy capable of interfering with the sensed signal. Automatic triggering events can also include a detected physiologic change such as a detected change in heart rate, a detected arrhythmia, a detected change in a respiratory rate, a detected change in neural traffic, a detected change in blood pressure, and a detected change in activity. Automatic triggering events can also be based on a timer or clock, such as a device with a controller and timer adapted to follow a circadian rhythm when switching modes. Examples of patient-actuated triggers include an external magnet 102 used to actuate a switch (e.g. reed switch) in the implantable device to switch modes, and a patient-actuated external programmer 103 that enables the patient to selectively choose the mode Co which the device should switch.

FIG. 1 also illustrates the IMD 101 communicating with an external device 103 such as a patient-actuated device capable of being used to change modes in the MID 101. A programmer, capable of providing all programming functions, including mode switching, can also be used to communicate with the MID. The patient-actuated device can be a stand-alone device designed to only provide the desired mode switching capabilities, or can be integrated into other devices. An example of a patient-actuated device includes a personal digital assistant or other electronic device such as would be used in an advanced patient management (APM) system, which can organize and perform calculations based on recorded data, and later provide the data to a programmer.

Figure 2:
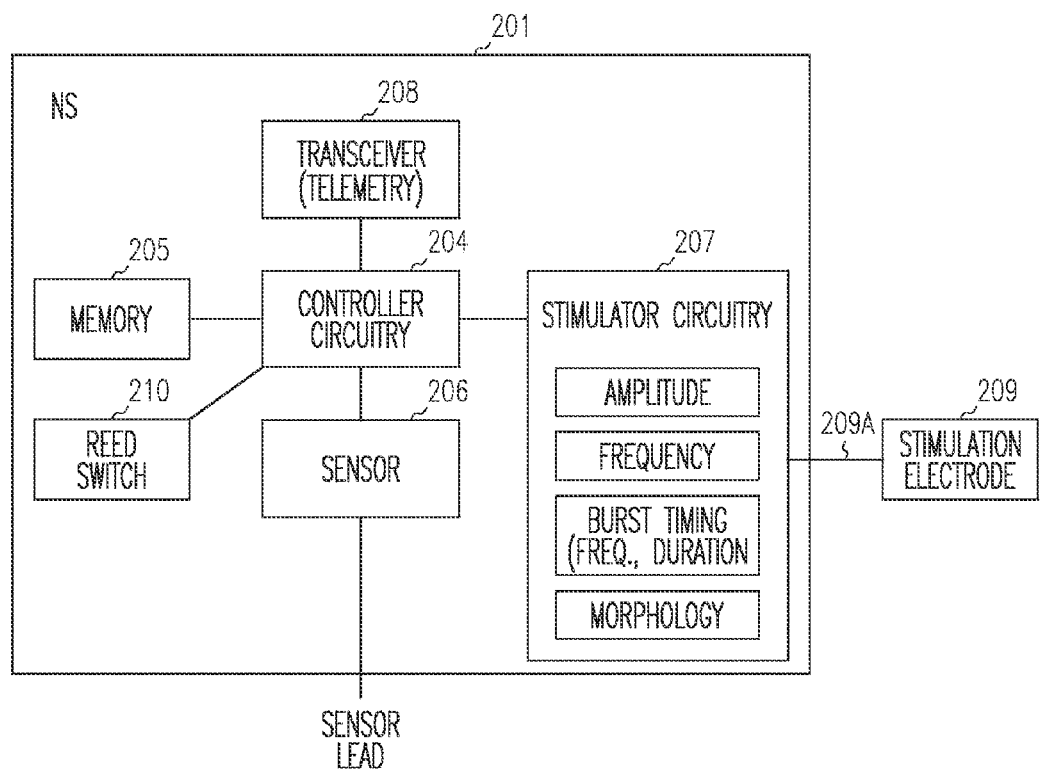
FIG. 2 illustrates an embodiment of an implantable neural stimulator (NS) device such as can be incorporated as the IMD in the system of FIG. 1.

FIG. 2 illustrates an embodiment of an implantable neural stimulator (NS) device 201 such as can be incorporated as the 111/ID 101 in the system 100 of FIG. 1. The illustrated neural stimulator 201 includes controller circuitry 204 connected to a memory 205, a sensor 206, neural stimulation circuitry 207, and a transceiver 208. An electrode 209 is connected to the stimulator circuitry 207 via a port 209A. The memory includes instructions or algorithms operated on by the controller and further includes parameters for use in the algorithms to provide the desired neural stimulation therapy. These instructions and parameters cooperate to operate the device in a mode. The device can be operated in different modes by operating on different instructions and/or parameters. Some embodiments use the sensor, such as a neural sensor or other physiologic sensor like a heart rate sensor, to provide feedback for the neural stimulation. The stimulator circuitry is adapted to adjust parameters of the neural stimulation signal transmitted to the electrode. According to various embodiments, one or more of the amplitude, the frequency, the morphology and the burst timing (frequency and duration of bursts) are capable of being adjusted. A magnetic-actuated switch 210, such as a reed switch, is connected to the controller for use to receive a user-provided trigger (e.g. flux from the external magnet) to switch modes. Modes can be switched via communications received through the transceiver 208 from the external device or can be automatically switched, such as if mode changes are based on a clock or other feedback. Historical data for mode switching events can be saved in memory 205. The external device can access the memory to display the data regarding the switching events, or can otherwise process the data for a variety of purposes.

Figure 3:
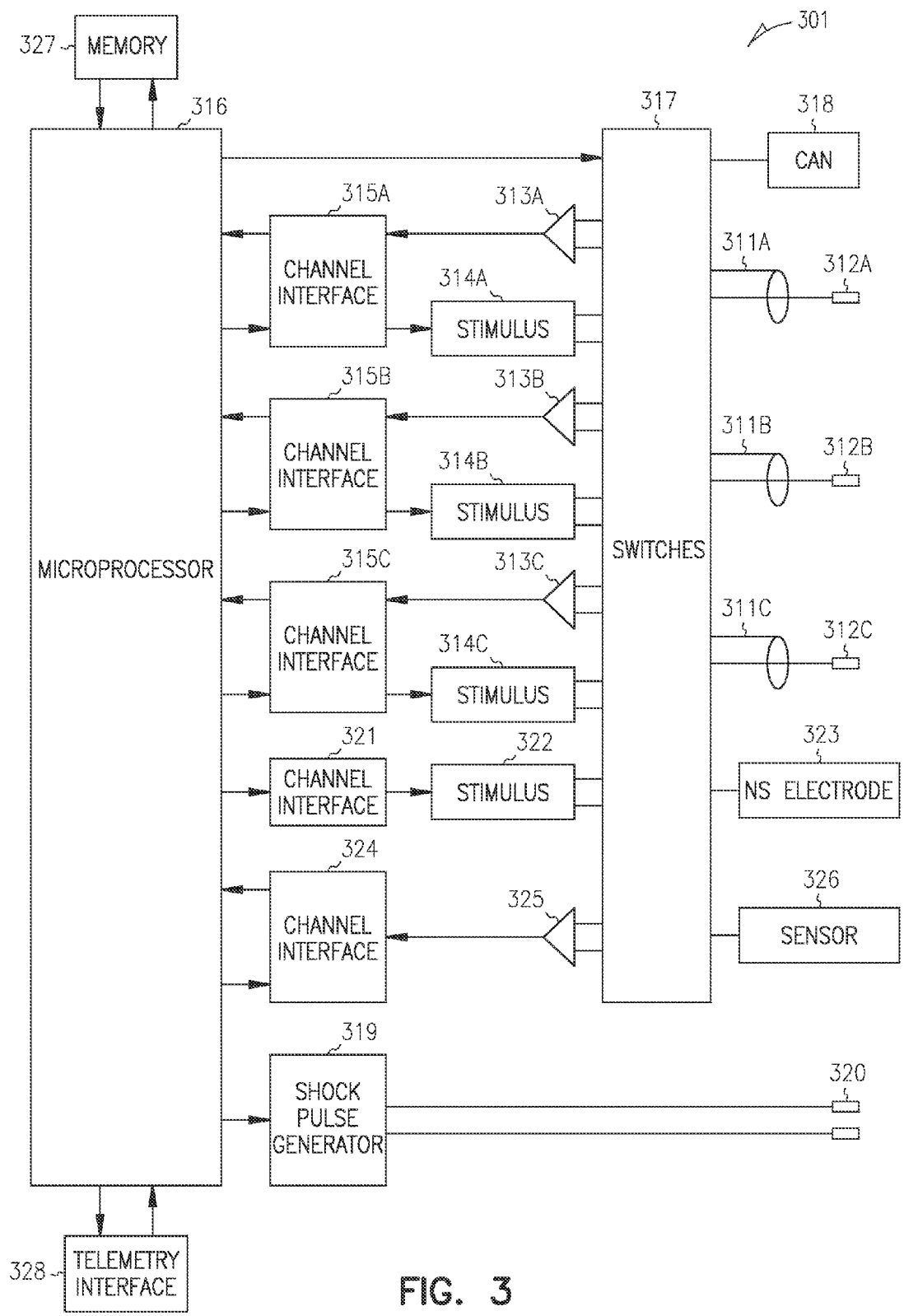
FIG. 3 illustrates a system diagram of an implantable medical device embodiment configured for multi-site stimulation and sensing.

FIG. 3 illustrates a system diagram of an implantable medical device embodiment configured for multi-site stimulation and sensing. This diagram provides another example of an IMD 301 capable of performing a number of neural stimulation and CRM therapies. Pacing, as used in the discussion of this figure, relates to electrical stimulation. In various embodiments, the stimulation for a given channel includes stimulation to capture myocardia, neural stimulation or both pacing and neural stimulation. Three examples of sensing and pacing channels are designated "A" through "C", and such channel can be used to stimulate a right atrium, a right ventricle and a la ventricle, for example. The illustrated channels comprise bipolar leads with ring electrodes 311A-C and tip electrodes 312A-C, sensing amplifiers 313A-C, pulse generators 314A-C, and channel interfaces 315A-C. Each of these channels includes a stimulation channel extending between the pulse generator the electrode and a sensing channel extending between the sense amplifier and the electrode. The channel interfaces 315A-C communicate bidirectionally with microprocessor 316, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry 313A-C detects a chamber sense, either an atrial sense or ventricular sense, when an electrogram signal (i.e., a voltage sensed by an electrode representing cardiac electrical activity) generated by a particular channel exceeds a specified detection threshold. Algorithms, including a number of adjustable parameters, used in particular modes can employ such senses to trigger or inhibit stimulation, and the intrinsic atrial and/or ventricular rates can be detected by measuring the time intervals between atrial and ventricular senses, respectively.

The switching network 317 is used to switch the electrodes to the input of a sense amplifier in order to detect intrinsic cardiac activity and to the output of a pulse generator in order to deliver stimulation. The switching network also enables the device to sense or stimulate either in a bipolar mode using both the ring and tip electrodes of a lead or in a unipolar mode using only one of the electrodes of the lead with the device housing or can 318 serving as a ground electrode or another electrode on another lead serving as the ground electrode. A shock pulse generator 319 is also interfaced to the controller for delivering a defibrillation shock via a pair of shock electrodes 320 to the atria or ventricles upon detection of a shockable tachyarrhythmia. Channel interface 321 and neural stimulation pulse generator 322 provide a connection between the microprocessor and the switch to deliver neural stimulation using the neural stimulation electrode 323. Channel interface 324 and sense amplifier 325 provide a connection between the microprocessor and the switch to receive a sensed signal from a sensor 326 for use to provide feedback for therapies such as a neural stimulation therapy.

The controller or microprocessor controls the overall operation of the device in accordance with programmed instructions and a number of adjustable parameters stored in memory 327, including controlling the delivery of stimulation via the channels, interpreting sense signals received from the sensing channels, and implementing timers for defining escape intervals and sensory refractory periods. The controller is capable of operating the device in a number of programmed stimulation modes which define how pulses are output in response to sensed events and expiration of time intervals. Most pacemakers for treating bradycardia are programmed to operate synchronously in a so-called demand mode where sensed cardiac events occurring within a defined interval either trigger or inhibit a pacing pulse. Inhibited stimulation modes utilize escape intervals to control pacing in accordance with sensed intrinsic activity such that a stimulation pulse is delivered to a heart chamber during a cardiac cycle only after expiration of a defined escape interval during which no intrinsic beat by the chamber is detected. Escape intervals for ventricular stimulation can be restarted by ventricular or atrial events, the latter allowing the pacing to track intrinsic atrial beats. A telemetry interface 328 is also provided which enables the controller to communicate with an external programmer or remote monitor.

Figure 4:
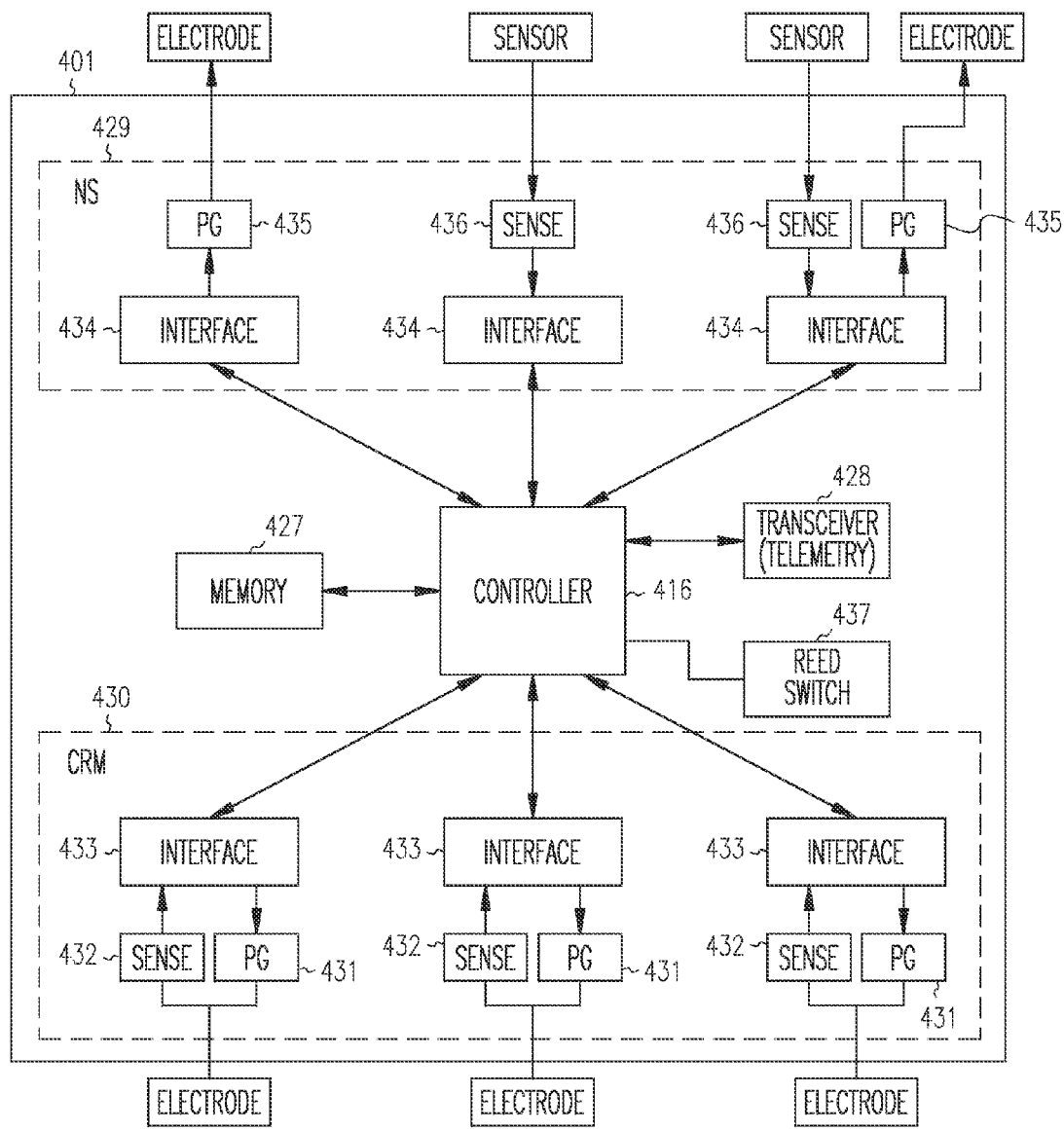
FIG. 4 illustrates an embodiment of an implantable medical device (IMD) such as shown in FIG. 1 having a neural stimulation (NS) component and cardiac rhythm management (CRM) component.

FIG. 4 illustrates an embodiment of an implantable medical device (IMD) 401 such as shown at 101 in FIG. 1 having a neural stimulation (NS) component 429 and cardiac rhythm management (CRM) component 430. The illustrated device 401 includes a controller 416 and a memory 427. According to various embodiments, the controller includes hardware, software, or a combination of hardware and software to perform the neural stimulation and CRM functions. For example, the programmed therapy applications, including various mode in which the device can operate, discussed in this disclosure are capable of being stored as computer-readable instructions embodied in memory and executed by a processor. According to various embodiments, the controller includes a processor to execute instructions embedded in memory to perform the neural stimulation and CRM functions. The illustrated device 401 further includes a transceiver 428 and associated circuitry for use to communicate with a programmer or another external or internal device. Various embodiments include a telemetry coil.

The CRM therapy section 430 includes components, under the control of the controller, to stimulate a heart and/or sense cardiac signals using one or more electrodes. The CRM therapy section includes a pulse generator 431 for use to provide an electrical signal through an electrode to stimulate a heart, and further includes sense circuitry 432 to detect and process sensed cardiac signals. An interface 433 is generally illustrated for use to communicate between the controller 416 and the pulse generator 431 and sense circuitry 432. Three electrodes are illustrated as an example for use to provide CRM therapy. Ports in the device provides signal channels from the device to the electrodes. The present subject matter is not limited to a particular number of electrode sites. Each electrode may include its own pulse generator and sense circuitry. However, the present subject matter is not so limited. The pulse generating and sensing functions can be multiplexed to function with multiple electrodes.

The NS therapy section 429 includes components, under the control of the controller, to stimulate a neural stimulation target and/or sense autonomic nervous system (ANS) parameters associated with nerve activity or surrogates of ANS parameters such as blood pressure and respiration. Three interfaces 434 are illustrated for use to provide ANS therapy. However, the present subject matter is not limited to a particular number interfaces, or to any particular stimulating or sensing functions. Pulse generators 435 are used to provide electrical pulses through a port to an electrode for use to stimulate a neural stimulation site. According to various embodiments, the pulse generator includes circuitry to set, and in some embodiments change, the amplitude of the stimulation pulse, the frequency of the stimulation pulse, the burst frequency of the pulse, and the morphology of the pulse such as a square wave, triangle wave, sinusoidal wave, and waves with desired harmonic components to mimic white noise or other signals. Sense circuits 436 are used to detect and process signals from a sensor, such as a sensor of nerve activity, blood pressure, respiration, and the like. The interfaces 434 are generally illustrated for use to communicate between the controller 416 and the pulse generator 435 and sense circuitry 436. Each interface, for example, may be used to control a separate lead. Various embodiments of the NS therapy section only include a pulse generator to stimulate a neural stimulation target.

According to various embodiments, the lead(s) and the electrode(s) on the leads are physically arranged with respect to the heart in a fashion that enables the electrodes to properly transmit pulses and sense signals from the heart, and with respect to neural targets to stimulate, and in some embodiments sense neural traffic from, the neural targets. Examples of neural targets include both efferent and afferent pathways, such as baroreceptors, nerve trunks and branches such as the vagus nerve, and cardiac fat pads, to provide a desired neural stimulation therapy. As there may be a number of leads and a number of electrodes per lead, the configuration can be programmed to use a particular electrode or electrodes.

The leads of the device include one or more leads to provide CRM therapy, such as atrial pacing, right and/or ventricular pacing, and/or defibrillation. The device also contains at least one neural stimulation lead which is placed in an appropriate location. Some embodiments perform neural stimulation and CRM therapy using the same lead. Examples of neural stimulation leads include: an expandable stimulation lead placed in the pulmonary artery in proximity of a high concentration of baroreceptors; an intravascularly-fed lead placed proximate to a cardiac fat pad to transvascularly stimulate the fat pad; an epicardial lead with an electrode placed in or proximate to the fat pad; a cuff electrode placed around the aortic, carotid, or vagus nerve; and an intravascularly-fed lead placed to transvascularly stimulate the aortic, carotid or vagus nerve. Other lead placements to stimulate other neural targets may be used.

The controller controls delivery of the electrical pulses, and is adapted to operate the device in a number of different modes. For example various embodiments switch between modes selected from the group consisting of a set of operation modes, a set of stimulation site modes and a set of feedback modes. In some embodiments, the group further consists of a set of therapy modes such that the device is able to switch between or among two or more therapy modes. Examples of operation modes includes a mode to provide neural stimulation and sensing, a mode to provide neural stimulation without sensing, and a mode to provide sensing without neural stimulation. Examples of stimulation site modes includes a mode to provide neural stimulation to a first neural stimulation site(s) or target(s) and a mode to provide neural stimulation to a second neural stimulation site(s) or target(s). Examples of feedback modes includes a mode to sense from a first site and a mode to sense from a second site, and also includes a mode to sense a first parameter and a mode to sense a second parameter. Examples of therapy modes include neural stimulation therapy, CRM therapy, drug therapy, and combinations thereof. In addition, various embodiments are also able to switch between various CRM therapy modes, such as atrial pacing (AOO, AAI), ventricular pacing (VVI, VOO), and or dual chamber pacing (DDI, DDD, VDD), for example. Additionally, changing modes includes changing parameters for a particular pacing mode, such as base rate, upper rate, AV interval, ventricular refractory and ventricular blanking in a DDD pacing mode.

The illustrated device 401 in FIG. 4 includes a switch 437, such as a reed switch, adapted to be actuated by magnetic flux from an external magnet positioned proximate to the device 401. The controller and switch are adapted to switch modes when magnetic flux actuates the switch. In various embodiments, a patient actuated programmer communicates with the controller through the transceiver to change modes. In various embodiments, the controller automatically changes the modes using, for example, a feedback signal or a timer. Historical data for mode switching events can be saved in memory 427. The external device can access the memory to display the data regarding the switching events, or can otherwise process the data for a variety of purposes.

Figure 5:
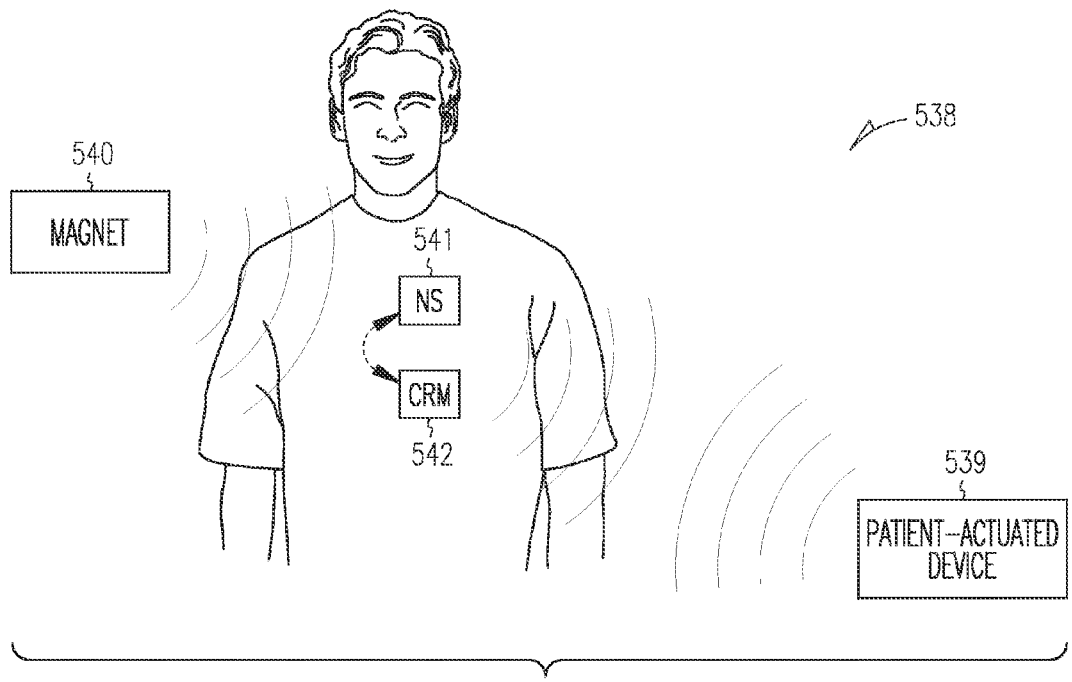
FIG. 5 illustrates a system including a patient-actuated external device, a magnet, an implantable neural stimulator (NS) device and an implantable cardiac rhythm management (CRM) device, according to various embodiments of the present subject matter.

FIG. 5 illustrates a system 538 including a patient-actuated external device 539, a magnet 540, an implantable neural stimulator (NS) device 541 and an implantable cardiac rhythm management (CRM) device 542, according to various embodiments of the present subject matter. Various aspects involve a method for communicating between an NS device and a CRM device or other cardiac stimulator. This communication allows one of the devices 541 or 542 to deliver more appropriate therapy (i.e. more appropriate NS therapy or CRM therapy) based on data and/or communication signals received from the other device. Some embodiments provide on-demand communications. The illustrated NS device and the CRM device are capable of wirelessly communicating with each other, and the programmer is capable of wirelessly communicating with at least one of the NS and the CRM devices. For example, various embodiments use telemetry coils to wirelessly communicate data and instructions to each other. In other embodiments, communication of data and/or energy is by ultrasonic means. In some embodiments, a lead provides a hardwired communication path between the two devices.

Figure 6:
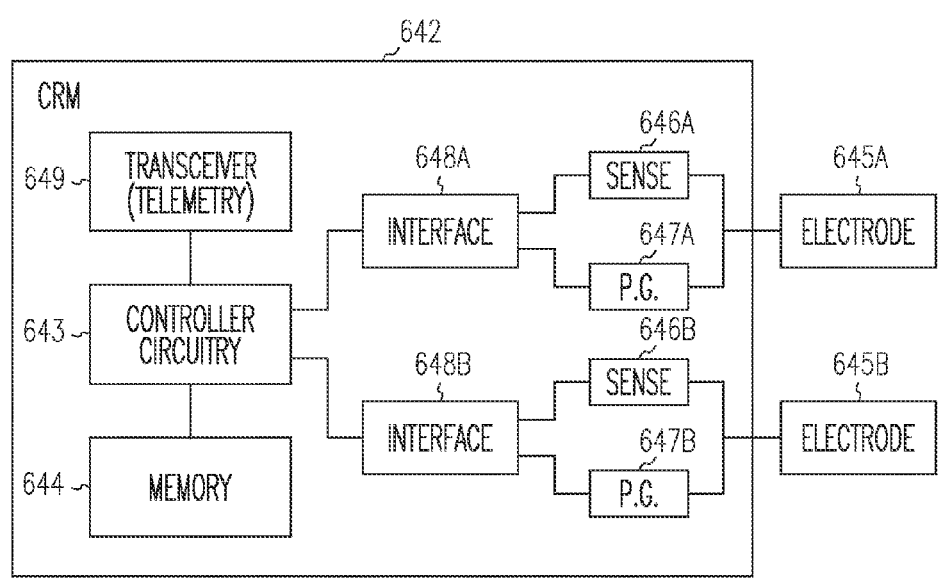
FIG. 6 illustrates an embodiment of CRM device, such as can be used in the system of FIG. 5.

FIG. 6 illustrates an embodiment of CRM device 642, such as can be used at 542 in the system of FIG. 5. The illustrated device 642 includes a controller 643 connected to a memory 644. The figure further illustrates electrodes 645A and 645B connected to the device. According to the illustration, the electrodes 645A and 645B are connected to sense modules 646A and 646B to sense electrical signal at the electrode, and pulse generators 647A and 647B to generate stimulation signals to the electrodes. The controller 643 is connected to the sense modules 646A and 646B and the pulse generator modules 647A and 647B via interfaces 648A and 648B.

The memory includes data and instructions. The controller is adapted to access and operate the instructions to perform various functions within the device, including programmed CRM therapies. The memory 644 includes a plurality of parameters that are used to control the delivery of the therapy using a number of modes. A transceiver 649 is connected to the controller 643. The CRM device is capable of wireless communicating with an external device, for example, using the transceiver 649. For example, various embodiments use telemetry coils to wirelessly communicate data and instructions. In other embodiments, communication of data and/or energy is by ultrasonic means.

Figure 7:
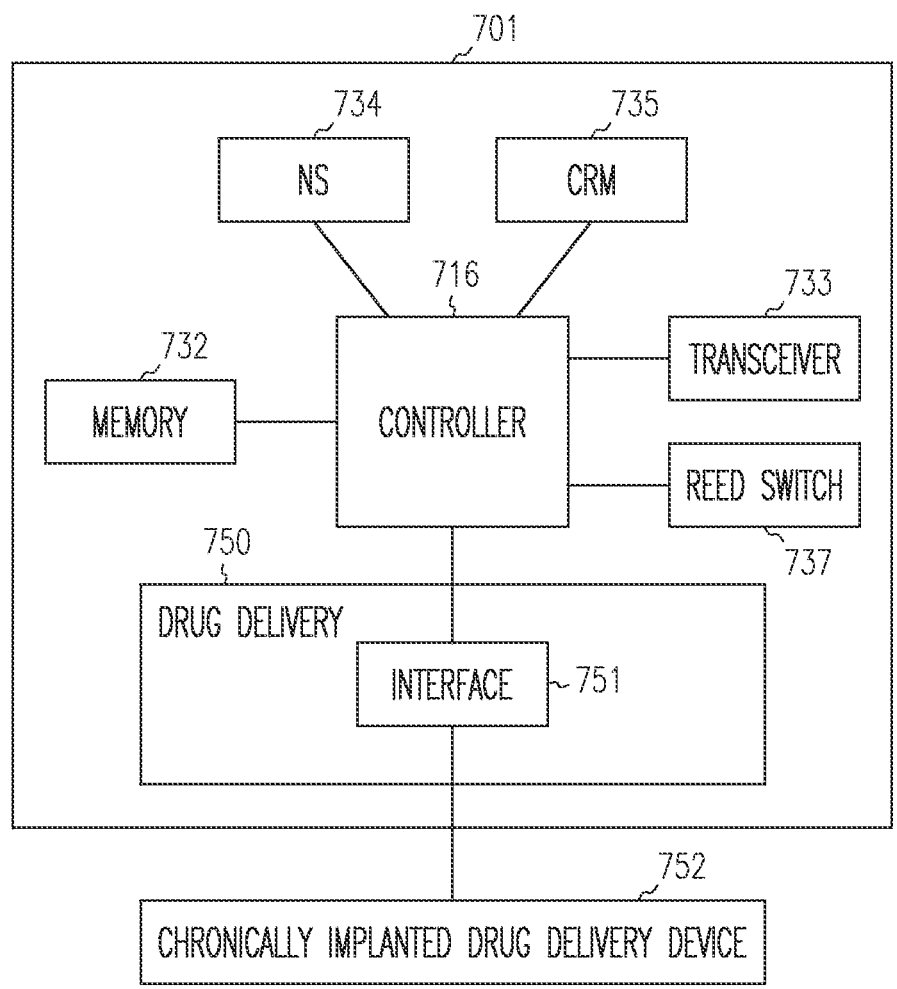
FIG. 7 illustrates an implantable medical device (IMD) such as shown in FIG. 1 having a neural stimulation (NS) component, a cardiac rhythm management (CRM) component, and a drug delivery component, according to various embodiments of the present subject matter.

FIG. 7 illustrates an implantable medical device (IMD) 701 such as shown at 101 in FIG. 1 having a neural stimulation (NS) component 734, a cardiac rhythm management (CRM) component 735, and a drug delivery component 750, according to various embodiments of the present subject matter. Examples of a NS component 734 and a CRM component 735 are illustrated in FIG. 4 at 429 and 430, respectively. The illustrated IMD 701 further includes a controller 716 connected to the therapy components 734, 735 and 750 to control the delivery of the therapies, and also includes a memory 732 to store instructions and data, a transceiver 733, and a magnetic-actuated switch, such as a reed switch 737. The drug delivery component 750 includes an interface 751 to provide an operable connection between the controller 716 and a chronically-implanted drug delivery device 752.

The device is capable of operating in different modes, and switching between or among two or more modes in response to a triggering event. The triggering event can be automatic. Examples of automatic triggering event include a timer or feedback signals from various sensors. The triggering event can be patient-actuated. One example of a patient-actuated triggering event includes a magnet positioned proximate to the reed switch 737 to toggle the device between or among the different modes. Another example of a patient-actuated triggering event includes a patient-actuated programmer that wirelessly communicates with the device through the transceiver 733 to change modes of operation. In various embodiments, the IMD 701 is adapted to respond to a triggering event by changing therapy modes among a neural stimulation therapy, a CRM therapy, a drug therapy, and various combinations thereof.

One embodiment of the drug delivery device carries the drug between a substructure and an electro-erodible overcoat layer; and another embodiment of the device carries the drug using a drug delivery "chip" that is separately prepared and subsequently attached to the device. The drug is released from the drug delivery chip through an electro-erodible release mechanism. Progressive drug release is provided by wells or regions that are selectively opened by explicitly addressing a given well or region, or by a more generalized progressive erosion of a tapered thickness electro-erodible overcoat layer. The erosion process can be open-loop where a well understood time-erosion behavior is known, or can be closed-loop where the erosion progress is monitored using the known relationship among current, voltage and erosion profile. Either process provides control of the eroded capping layer and consequent drug release.

One embodiment of the drug release chip includes an array of well-like structures constructed so as to laterally isolate one well from another well so that one well is able to be selectively exposed using an electro-erodible process, for example, to deliver a specific drug type and drug dose. An electrically insulating layer covers the well(s) and the surrounding regions. One or more drugs are contained within the well(s). A cap layer of electro-erodible material covers the well(s). The electro-erodible material is non-toxic to the host biosystem both before and after electro-erosion. One example of an electro-erodible material is gold. The connections and cap layer can be patterned to allow individual well caps to be selected for electro-erosion using addressing logic. An electrically insulating, passivation covering insulates all interconnections except the intended electro-erosion region over and perhaps immediately around the drug release well. Alternatively, one or more thickness-graded capping layer(s) are selectively and progressively electro-eroded resulting in controlled progressive exposure of wells in the thinner capped region first. In various embodiments, a current, for a voltage-activated electro-erosion process, or a developed potential, for a current-activated electro-erosion process, are monitored to control the electro-erosion process.

Figure 8:
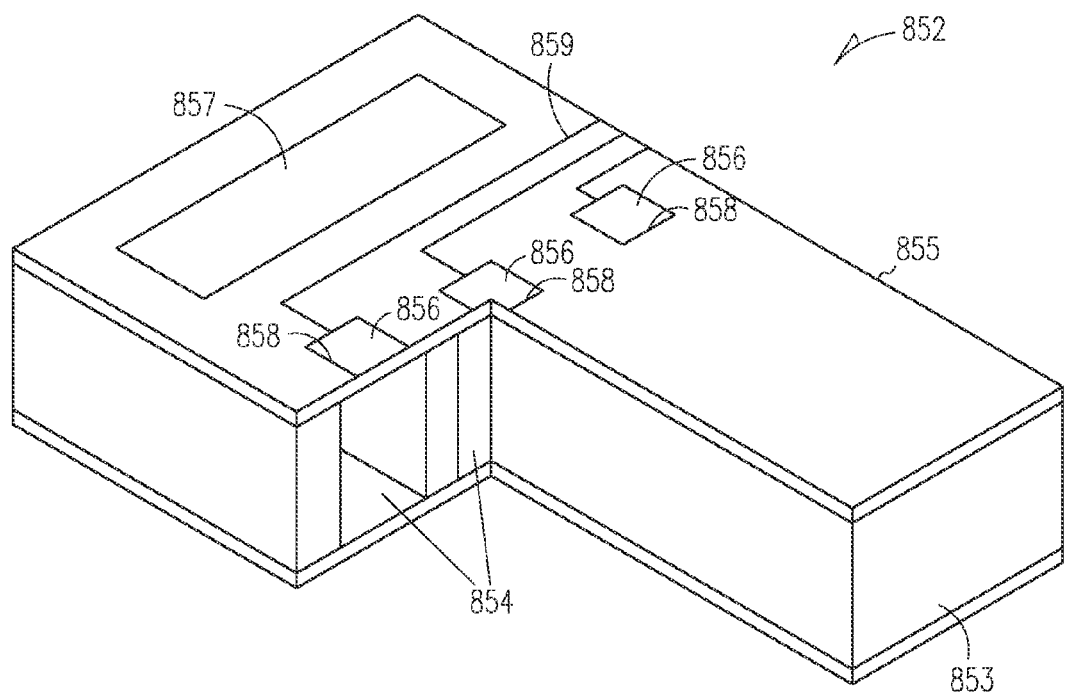
FIG. 8 illustrates one embodiment of a drug delivery microchip for use in one embodiment of a drug-eluting intravascular device.

FIG. 8 illustrates one embodiment of a drug delivery microchip 852 for use in one embodiment of a drug-eluting intravascular device. According to this embodiment, a silicon substrate 853 is formed with voids, wells or micro-reservoirs 854. These micro-reservoirs 854 have a sufficient size, are appropriately lined and are otherwise adapted to store an active substance (e.g. drug) to be released into a biosystem. A coating 855 is formed over the silicon substrate. Electro-erodible caps 856 are formed in the coating over the wells such that, upon being eroded, an opening is formed between the well and the surrounding biosystem. At least one cathode 857 and least one anode 858 are formed in coating 855. According to one embodiment, the at least one anode forms the electro erodible cap 856. Wiring 859 is used to control, or address, the anode to be electro eroded.

Figure 9:
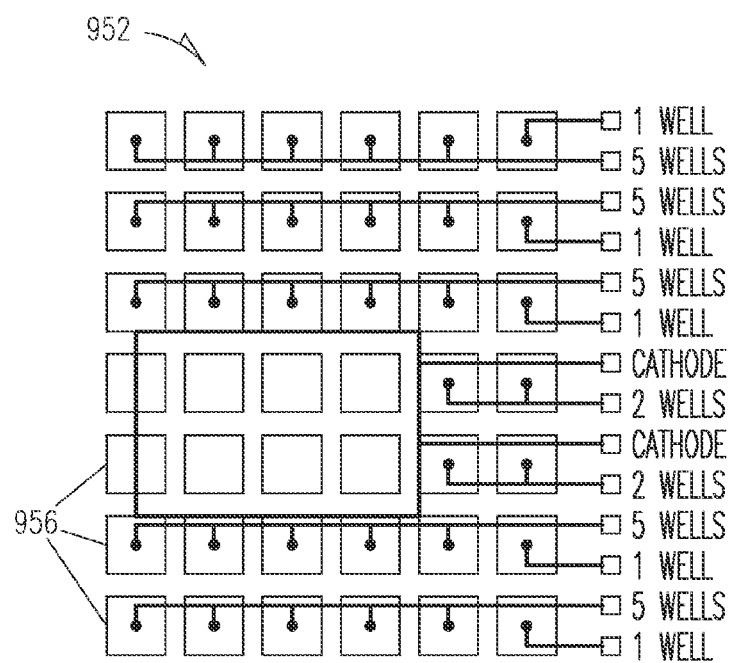
FIG. 9 illustrates one embodiment of a drug delivery microchip capable of delivering different drugs and different dosages of the drugs.

FIG. 9 illustrates one embodiment of a drug delivery microchip 952 capable of delivering different drugs and different dosages of the drugs. The wells within the microchip are addressable; that is, addressable control lines are used to select the wells or well-combinations whose caps 956 are to be electro eroded to elute the active substance contained therein. In the illustrated electrode configuration, there are five sets of one well, five sets of five wells and two sets of two wells. The different sized sets provide different delivery dosages. Alternatively, the physical size of the wells themself are used to control the delivery dosage. Additionally, different drug types are able to be stored in the different sets of wells, such that a desired drug among several is able to be dispensed upon the detection of a particular event.

Figure 10:
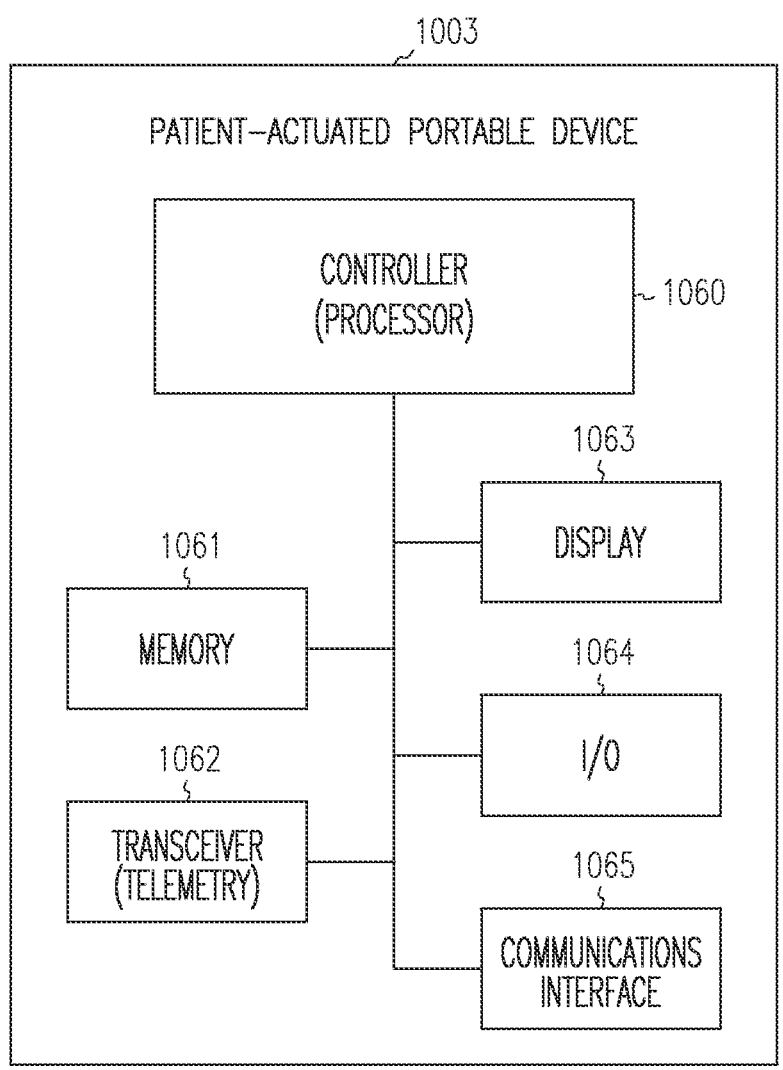
FIG. 10 illustrates a patient-actuated programmer, such as the external patient-actuated device illustrated in the system of FIG. 1, or other external device to communicate with the implantable medical device(s), according to various embodiments of the present subject matter.

FIG. 10 illustrates a patient-actuated programmer 1003, such as the external patient-actuated device 103 illustrated in the system of FIG. 1, or other external device to communicate with the implantable medical device(s), according to various embodiments of the present subject matter. An example of an external device includes Personal Digital Assistants (PDAs) or personal laptop and desktop computers in an Advanced Patient Management (APM) system. The illustrated device includes controller circuitry 1060 and a memory 1061. The controller circuitry is capable of being implemented using hardware, software, and combinations of hardware and software. For example, according to various embodiments, the controller circuitry includes a processor to perform instructions embedded in the memory to perform a number of functions, including communicating data and/or programming instructions to the implantable devices. According to some embodiments, such instructions include instructions for the device to change modes. The illustrated device 1003 further includes a transceiver 1062 and associated circuitry for use to communicate with an implantable device. Various embodiments have wireless communication capabilities. For example, various embodiments of the transceiver and associated circuitry include a telemetry coil for use to wirelessly communicate with an implantable device. The illustrated device 1003 further includes a display 1063, input/output (I/O) devices 1064 such as a display, keyboard, mouse/pointer and/or touch screen, and a communications interface 1065 for use to communicate with other devices, such as over a communication network. The patient-actuated device is able to communicate a trigger command to the IMD to switch to another mode of operation. In an embodiment of the patient-actuated programmer, the instructions contained in memory and operated on by the controller are appropriate to provide a user-friendly interface, with appropriate logical security to prevent inappropriate mode changes, to allow the user to change or otherwise select the modes for the IMD.

Figure 11:
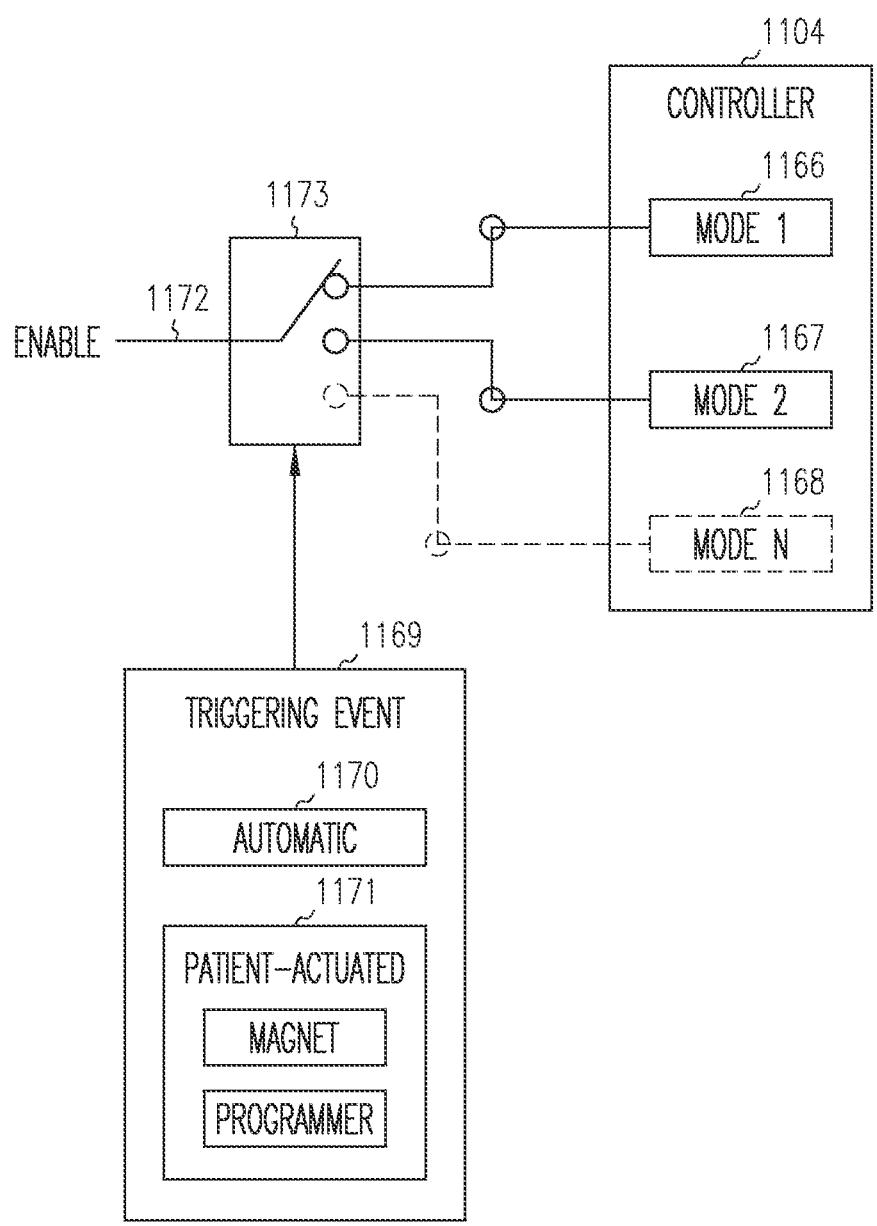
FIG. 11 illustrates an embodiment of a responsive relationship of an MID controller to a triggering event.

FIG. 11 illustrates an embodiment of a responsive relationship of an IMD controller to a triggering event. The illustration includes a controller 1104 adapted to operate the IMD in a first mode 1166, a second mode 1167 and an Nth mode 1168. The illustration further includes a representation of a triggering event 1169, which can be an automatic event 1170 and/or a patient-actuated event 1171 such as a magnet moved proximate to a reed switch or a patient-actuated programmer. Examples of automatic triggering events include a detected device change such as a detected electrode failure, an End Of Life (EOL) determination for a battery to power the device, a detected lead failure, an environmental change like a detected electrical interference that is capable of interfering with the sensed signal or the application of another therapy capable of interfering with the sensed signal. Automatic triggering events can also include a detected physiologic change such as a detected change in heart rate, a detected arrhythmia, a detected change in a respiratory rate, a detected change in neural traffic, a detected change in blood pressure, and a detected change in activity. Automatic triggering events can also be based on a timer or clock, such as a device with a controller and timer adapted to follow a circadian rhythm when switching modes. The illustration also includes an enable signal 1172 connected to the controller to enable a mode of operation via a switch 1173. The triggering event is adapted to control the switch 1173 to selectively enable a mode of operation by the controller 1104. The illustrated responsive relationship can be performed in hardware, software, or a combination thereof.

Figure 12:
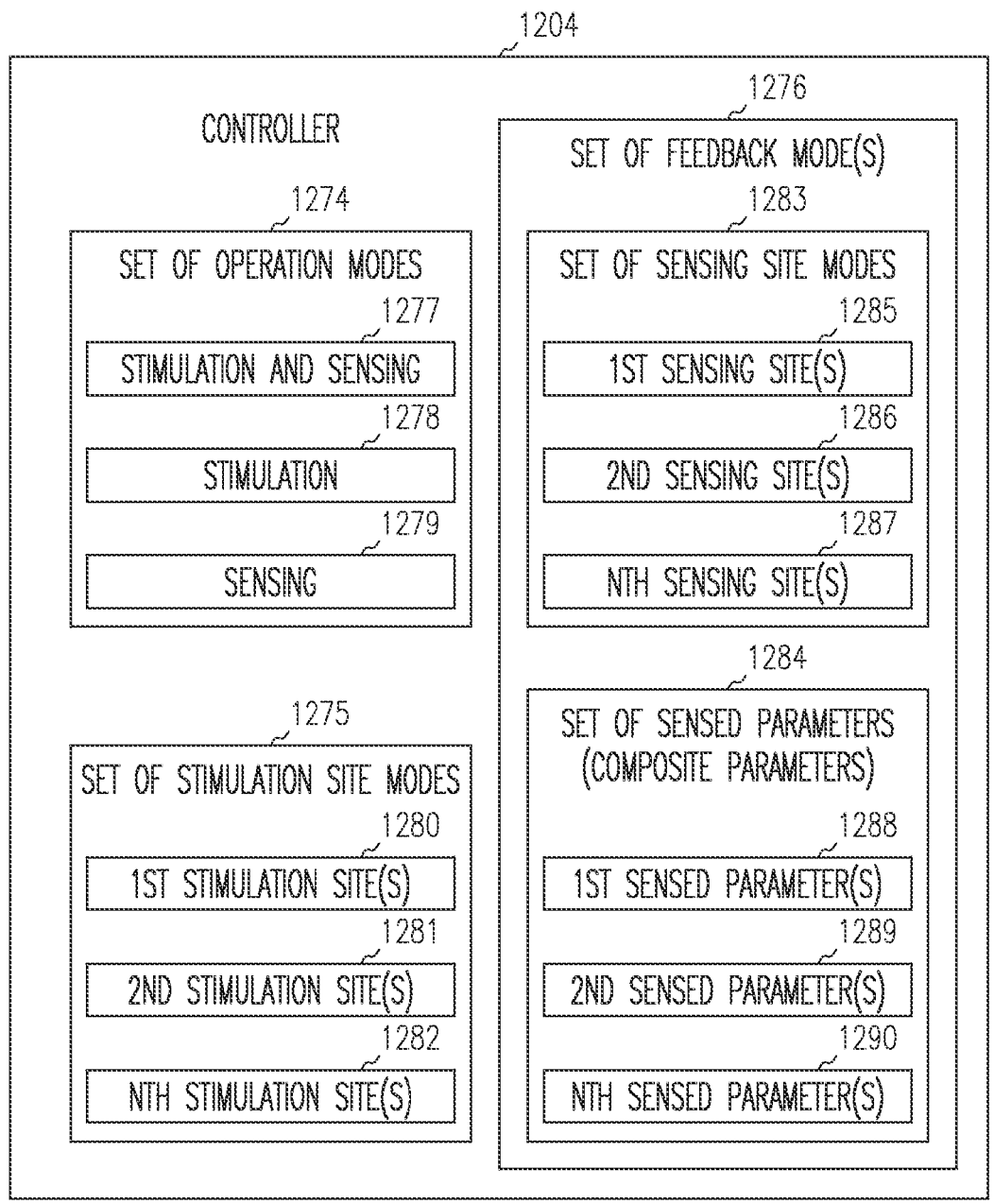
FIG. 12 illustrates an embodiment of a controller capable of switching modes within a set of operation modes, a set of stimulation site modes, and a set of feedback modes.

FIG. 12 illustrates an embodiment of a controller 1204 capable of switching modes within a set of operation modes 1274, a set of stimulation site modes 1275, and a set of feedback modes 1276. With respect to the set of operation modes 1274, the illustrated controller 1204 is adapted to switch between or among two or more modes. An example of an application for switching modes within a set of operation modes 1274 includes switching between therapy and diagnostic modes in response to noise. Examples of modes within the set of operation modes 1274 includes a stimulation and sensing mode 1277 in which closed-loop neural stimulation is provided to neural target(s) based on sensed parameters, a stimulation mode 1278 in which open-loop neural stimulation is provided to neural target(s), and a sensing mode 1279 in which neural stimulation is not provided to neural target(s) but sensing processes continue. Examples of sensed parameters include, but are not limited to, blood pressure, heart rate, and nerve traffic.

With respect to the set of stimulation site modes 1275, the illustrated controller 1204 is adapted to switch between or among two or more stimulation site modes. Examples of applications for switching stimulation site modes 1275 includes switching between parasympathetic and sympathetic nerve stimulation to treat tachycardia-bradycardia syndrome, switching from afferent to efferent stimulation, and changing the dose of the neural stimulation therapy by changing the number of stimulation sites. For example, the illustrated controller is adapted to switch among a mode to stimulate a first stimulation site or sites 1280, a mode to stimulate a second stimulation site or sites 1281, and a mode to stimulate an Nth stimulation site or sites 1282.

With respect to the set of feedback modes 1276, the illustrated controller is adapted to switch among sensing site modes 1283 and to switch among sensed parameter and/or composite parameter modes 1284. Composite parameters are parameters based on two or more other parameters. Examples of applications for switching among sensing site modes 1283 includes recording parasympathetic or sympathetic traffic, recording afferent or efferent traffic, and switching from atrial to ventricular rhythm monitoring. Examples of applications for switching among sensed parameter/composite parameter modes 1284 include detecting short-term brief events such as an impulse burst versus a time-averaged long-term signal trend, and detecting impulse duration versus impulse magnitude. The illustrated controller is adapted to switch among a first site 1285, a second site 1286 and an Nth site 1287 from which to provide sensing for a feedback signal, and is also adapted to switch among a first sensed parameter 1288, a second sensed parameter 1289 and an Nth sensed parameter 1290. Thus, although the sensing site may not change, a different parameter can be detected.

Figure 13:
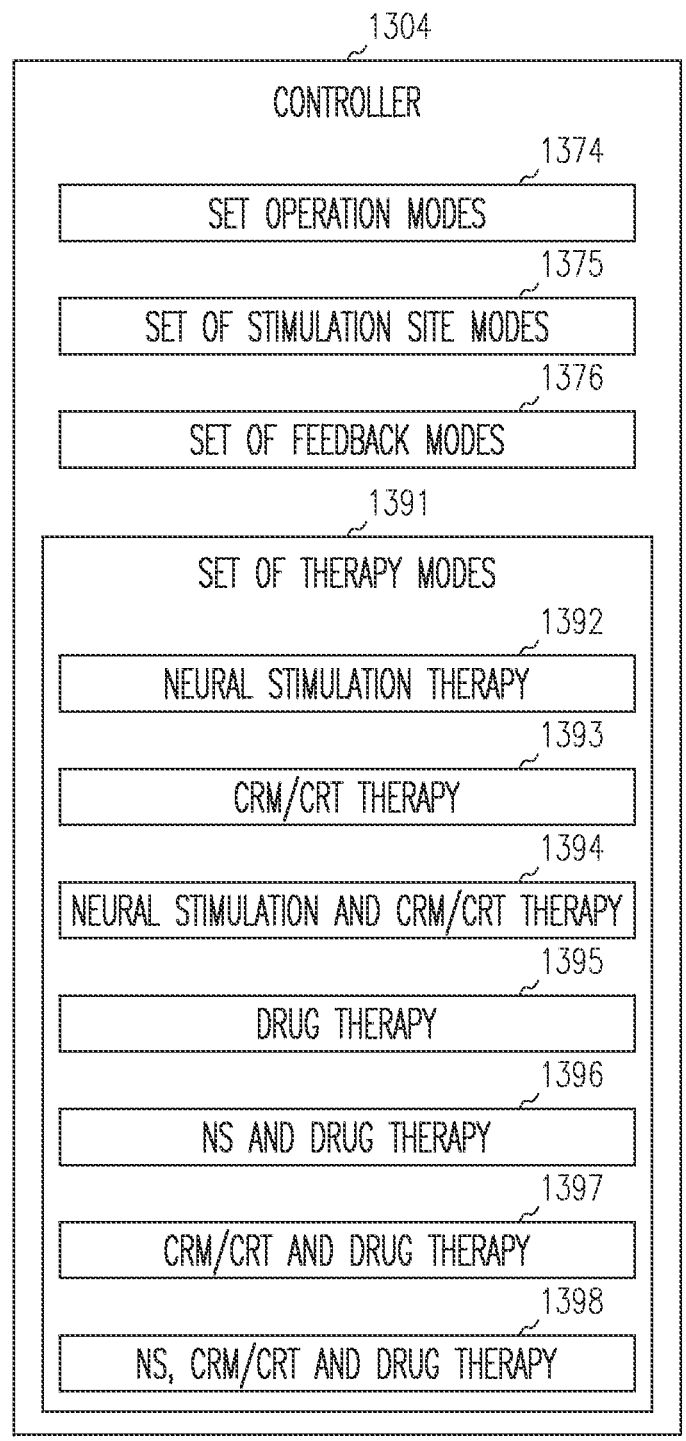
FIG. 13 illustrates an embodiment of a controller capable of switching modes within a set of operation modes, a set of stimulation site modes, a set of feedback modes, and a set of therapy modes.

FIG. 13 illustrates an embodiment of a controller 1304 capable of switching modes within a set of operation modes 1374, a set of stimulation site modes 1375, a set of feedback modes 1376, and a set of therapy modes 1391. Examples of modes 1374, 1375 and 1376 are provided in FIG. 12 at 1274, 1275 and 1276. With respect to the set of therapy modes 1391, the illustrated controller 1304 is adapted to switch between or among two or more modes. Examples of modes within the set of therapy modes includes a neural stimulation therapy mode 1392, a cardiac rhythm management and/or cardiac resynchronization therapy (CRM/CRT) mode 1393, a neural stimulation and CRM therapy mode 1394, a drug therapy mode 1395, a neural stimulation and drug therapy mode 1396, a CRM/CRT and drug therapy mode 1397, and a neural stimulation, CRM/CRT and drug therapy mode 1398. An example of a neural stimulation mode 1392 includes an anti-remodeling, vagal nerve stimulation therapy. An example of a CRM/CRT therapy 1393 includes a resynchronization therapy for a heart failure patient to improve the pumping function of the left ventricle. Examples of a neural stimulation and a CRM/CRT therapy 1394 include a vagal nerve stimulation therapy and anti-tachycardia pacing to terminate arrhythmia, and vagal nerve stimulation in anticipation of a defibrillation shock to reduce the defibrillation threshold. An example of a drug therapy mode 1395 includes an angiogenic growth factor release to treat ischemia. An example of a neural stimulation and a drug therapy mode 1396 includes vagal nerve stimulation and delivery of an angiogenic drug to promote cardiac muscle repair after an myocardial infarction. An example of a CRM/CRT and drug therapy includes pacing to unload a region of a heart damaged by a myocardial infarction such that the damaged heart region works less and delivery of an angiogenic drug to promote cardiac muscle repair. An example of a neural stimulation, CRM/CRM and drug therapy 1398 includes vagal nerve stimulation, pacing to unload a region of a heart damaged by a myocardial infarction, and delivery of an angiogenic drug to prevent post myocardial infarction remodeling.

One of ordinary skill in the art will understand that, the modules and other circuitry shown and described herein can be implemented using software, hardware, and combinations of software and hardware. As such, the illustrated modules and circuitry are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. With reference to FIG. 5, for example, some embodiments use sensed activity, such as sensed neural activity, in a neural stimulation device to switch modes for a CRM device. The sensed data in the neural stimulation device can be used to alter the mode, rate, AV delay, VV delay, tachyarrhythmia parameters, and various combinations thereof. Some embodiments allow data sensed in a CRM device to mode switch a neural stimulation device.

In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed is:

1. A system for using at least one electrode to deliver vagal nerve stimulation therapy to vagus nerve in a patient, comprising:

an implantable device configured to be implanted in the patient, comprising:
stimulation circuitry configured to use the at least one electrode to deliver electrical stimulation to the vagus nerve;
memory including sets of programmed instructions stored therein to operate the device to deliver the vagal nerve stimulation in at least two different operating modes, wherein the implantable device is configured to change operating modes in response to an external signal, each of the at least two different operating modes is used to deliver vagal nerve stimulation therapy, and the sets of programmed instructions are concurrently in the memory and include different sets of programmed instructions to operate the device to deliver the vagal nerve stimulation therapy; and
a controller connected to the memory and the stimulation circuitry to control the stimulation circuitry, the controller configured to control delivery of the electrical stimulation for the neural stimulation therapy including change adjustable parameters to control delivery of the electrical stimulation for the neural stimulation therapy, the controller configured to execute the programmed instructions in the memory to operate the device to deliver the vagal nerve stimulation therapy in the at least two operating modes, the controller configured to receive the external signal transmitted from an external device external to the patient and respond to the received external signal by changing from executing one set of programmed instructions to operate the device to deliver the vagal nerve stimulation therapy in one of the operating modes to executing another, different set of programmed instructions to operate the device to deliver the vagal nerve stimulation therapy in another one of the operating modes.

2. The system of claim 1, wherein the controller is configured to receive a magnetic signal transmitted from the external device, and respond to the received magnetic signal by changing from executing one set of programmed instructions to operate the device to deliver the vagal nerve stimulation therapy in one of the operating modes to executing the other, different set of programmed instructions to operate the device to deliver the vagal nerve stimulation therapy in the other one of the operating modes.

3. The system of claim 1, wherein the at least one electrode includes an electrode configured to be placed around the vagus nerve.

4. The system of claim 1, wherein the at least one electrode includes an intravascular electrode configured to stimulate the vagus nerve.

5. The system of claim 1, wherein the controller is configured to change a dose of the neural stimulation therapy when executing the other, different set of programmed instructions to operate the device to deliver the vagal nerve stimulation therapy in the other one of the operating modes.

6. The system of claim 5, wherein the controller is configured to change stimulation sites to change the dose of the neural stimulation therapy.

7. The system of claim 1, wherein one of the different sets of programmed instructions includes programmed instructions to operate the device to deliver afferent vagal nerve stimulation, and the other set of programmed instructions includes programmed instructions to operate the device to deliver efferent vagal nerve stimulation.

8. The system of claim 1, wherein the system is configured to sense a physiological signal, wherein the operating modes include at least two modes selected from the group of modes consisting of:
a stimulation and sensing mode, a stimulation mode in which the neural stimulation therapy is provided without using the sensed signal, and a sensing mode in which the neural stimulation therapy is not provided to the neural stimulation target.

9. The system of claim 1, wherein one of the operating modes includes stimulation of the vagus nerve using the at least one electrode, and another operating mode includes stimulation of the vagus nerve using at least one other additional electrode.

10. The system of claim 1, wherein the operating modes include sensing at a first sensing site and sensing at a second sensing site.

11. The system of claim 10, wherein sensing includes sensing at least one of blood pressure, heart rate or nerve traffic.

12. The system of claim 1, wherein the operating modes include parasympathetic stimulation and sympathetic stimulation.

13. A system for using at least one electrode to deliver vagal nerve stimulation therapy to vagus nerve in a patient, comprising:
a patient-actuated external device configured to deliver a wireless signal; and
an implantable device configured to be implanted in the patient, comprising:
stimulation circuitry configured to use the at least one electrode to deliver electrical stimulation to the vagus nerve;
memory including sets of programmed instructions stored therein to operate the device to deliver the vagal nerve stimulation in at least two different operating modes, wherein the implantable device is configured to change operating modes in response to the wireless signal, each of the at least two different operating modes is used to deliver vagal nerve stimulation therapy, and the sets of programmed instructions are concurrently in the memory and include different sets of programmed instructions to operate the device to deliver the vagal nerve stimulation therapy; and
a controller connected to the memory and the stimulation circuitry to control the stimulation circuitry, the controller configured to control delivery of the electrical stimulation for the neural stimulation therapy including change adjustable parameters to control delivery of the electrical stimulation for the neural stimulation therapy, the controller configured to execute the programmed instructions in the memory to operate the device to deliver the vagal nerve stimulation therapy in the at least two operating modes, the controller configured to receive the wireless signal transmitted from the external device and respond to the received wireless signal by changing from executing one set of programmed instructions to operate the device to deliver the vagal nerve stimulation therapy in an operating mode to executing another, different set of programmed instructions to operate the device to deliver the vagal nerve stimulation therapy in another operating mode.

14. The system of claim 13, wherein the wireless signal includes a magnetic signal.

15. The system of claim 13, wherein the patient-actuated external device includes a magnet.

16. The system of claim 13, wherein the patient-actuated external device includes a programmer.

17. The system of claim 13, wherein the at least one electrode includes an electrode configured to be placed around the vagus nerve.

18. The system of claim 13, wherein the controller is configured to change a dose of the neural stimulation therapy when executing the other, different set of programmed instructions to operate the device to deliver the vagal nerve stimulation therapy in the other operating mode.

19. The system of claim 13, wherein one of the different sets of programmed instructions includes programmed instructions to operate the device to deliver afferent stimulation of the vagus nerve, and the other set of programmed instructions includes programmed instructions to operate the device to deliver efferent stimulation.

20. The system of claim 13, wherein one of the operating modes includes stimulation of the vagus nerve using the at least one electrode, and another operating mode includes stimulation of the vagus nerve using at least one other additional electrode.

* * * * *